(12) United States Patent
Suzuki

(10) Patent No.: US 8,877,737 B2
(45) Date of Patent: Nov. 4, 2014

(54) ALLERGY INHIBITOR

(75) Inventor: Kengo Suzuki, Bunkyo-ku (JP)

(73) Assignee: Euglena Co., Ltd., Tokyo (JP)

( * ) Notice: Subject to any disclaimer, the term of this patent is extended or adjusted under 35 U.S.C. 154(b) by 0 days.

(21) Appl. No.: 13/583,175

(22) PCT Filed: Mar. 8, 2011

(86) PCT No.: PCT/JP2011/055389
§ 371 (c)(1),
(2), (4) Date: Sep. 6, 2012

(87) PCT Pub. No.: WO2011/111707
PCT Pub. Date: Sep. 15, 2011

(65) Prior Publication Data
US 2012/0329752 A1    Dec. 27, 2012

(30) Foreign Application Priority Data
Mar. 9, 2010   (JP) ................................. 2010-052072

(51) Int. Cl.
| | | |
|---|---|---|
| *A61K 31/716* | (2006.01) | |
| *A61K 31/715* | (2006.01) | |
| *C08B 37/00* | (2006.01) | |
| *A61P 37/08* | (2006.01) | |

(52) U.S. Cl.
CPC ........... *A61K 31/716* (2013.01); *C08B 37/0024* (2013.01)
USPC ....................................... 514/54; 536/123.12

(58) Field of Classification Search
USPC ....................................... 514/54; 536/123.12
See application file for complete search history.

(56) References Cited

U.S. PATENT DOCUMENTS 5,043,310 A * 8/1991 Takeuchi et al. ............... 502/404
2003/0203016 A1   10/2003 Suwelack et al.

FOREIGN PATENT DOCUMENTS

| JP | 2003-529538 A | 10/2003 |
|---|---|---|
| JP | 2004-339113 A | 12/2004 |

OTHER PUBLICATIONS

Sugiyama, Akihiko et al. (The Journal of veterinary medical science / the Japanese Society of Veterinary Science, (Jun. 2010) vol. 72, No. 6, pp. 755-63. Electronic Publication Date: Feb. 16, 2010).*
Sugiyama, Akihiko, et al., "Oral Administration of Paramylon, a β-1, 3-D-Glucan Isolated from *Euglena gracilis* Z Inhibits Development of Atopic Dermatitis-Like Skin Lesions in NC/Nga Mice,"Journal of Veterinary Medical Science, 2010, pp. 755-763, vol. 72, No. 6.
International Search Report for PCT/JP2011/055389, dated May 17, 2011.

* cited by examiner

*Primary Examiner* — Shaojia Anna Jiang
*Assistant Examiner* — Michael C Henry
(74) *Attorney, Agent, or Firm* — Sughrue Mion, PLLC

(57) ABSTRACT

The present invention provides an allergy inhibitor using the efficacy of amorphous paramylon which is a substance obtained by changing the crystalline structure of paramylon. The present invention relates to a substance for inhibiting allergic diseases. Amorphous paramylon of the present invention is an allergy inhibitor comprising amorphous paramylon which is obtained by amorphosizing crystalline paramylon derived from Euglena, and has a relative crystallinity of 20% or lower to the crystallinity of crystalline paramylon, determined by an X-ray diffractometry. This allergy inhibitor enables efficacious inhibition of allergic diseases such as atopic dermatitis, pollinosis, and the like.

3 Claims, 11 Drawing Sheets

Effects of Paramylon on TNCB-induced Dermatitis

FIG. 8 Histopathological Properties of Auricular Skin

ALLERGY INHIBITOR

CROSS REFERENCE TO RELATED APPLICATIONS

This application is a National Stage of International Application No. PCT/JP2011/055389 filed on Mar. 8, 2011, which claims priority from Japanese Patent Application No. 2010-052072, filed on Mar. 9, 2010, the contents of all of which are incorporated herein by reference in their entirety.

FIELD OF THE INVENTION

The present invention relates to an allergy inhibitor using an efficacy of amorphous paramylon which is obtained by changing a crystalline structure of paramylon.

Related Art

Atopic dermatitis, which is one of allergic diseases, is considered to produce a pruritic dermatological symptom caused by an acquisition of allergic reaction to environmental antigens (house dust, pollen, mold, or the like) and also by the associated overresponse to such antigens.

A sensitization to these allergens is established when an antigen-presenting cell phagocytoses an antigen and presents antigen information to a Th2 Type CD4+T cell, and then the Th2 Type CD4+T cell recognizes the antigen according to the antigen information.

In one case, a Th2 Type CD4+T cell infiltrating to a skin lesion produces a cytokine, which induces inflammation (Type IV hypersensitivity), and in another case, an inflammatory reaction is caused by degranulation of a mast cell in the peripheral tissue where the Th2 Type CD4+T cell further moved to a lymph node is sensitized with IgE of B cell (Type I hypersensitivity).

Both of the Type I hypersensitivity and the Type IV hypersensitivity are involved in atopic dermatitis in human and animals.

In recent years, it has been reported that β-1,3-glucan has an immunomodulatory function, and shows an effect of mitigating symptoms of pollinosis in human, but few reported the immunomodulatory effect of β-1,3-glucan and the detail has not yet been clarified.

Meanwhile, a polysaccharide derived from a microorganism called paramylon is generally known as β-1,3-glucan.

Paramylon has a polymer body produced by being polymerized with approximately 700 glucoses through β-1,3-bond, and contained in Euglena as a storage polysaccharide.

Paramylon is isolated from Euglena and used in various applications.

Such isolated paramylon granules are proved to have an efficacious action on human body and thus used for food.

For example, it is said that paramylon granules having a porous structure have an effect of adsorbing cholesterols and the like and excreting them out of the body.

Paramylon granules consisted of fine particles are also expected to be applied for cosmetics or other daily necessities.

Furthermore, as described above, it has been confirmed that β-1,3-glucan acts on the somatic immune system and shows various efficacy such as antibacterial effect, antiviral effect, metabolism improving effect, antitumor activity and antiallergic activity; and studies for utilizing such efficacy have also been in progress.

Under such circumstances, health foods and supplements containing paramylon isolated from Euglena have been developed, and as well, techniques for utilizing paramylon in various applications such as medicines have also been developed.

As an example, Patent Document 1 discloses a technique for preparing a freeze-dried medicine containing paramylon.

In the technique described in Patent Document 1, a medicine for parenteral or oral administration containing paramylon, which is isolated from cultured Euglena cells, is produced.

The medicine is used in a biological matrix, particularly as a plaster or a nutritional supplement, and also used as a cosmetic ingredient, or administered as a pharmaceutical ingredient.

Patent Document 2 discloses a technique for incorporating β-1,3-glucan produced by Euglena protozoa as an ingredient for mitigating dermatosis such as skin roughness.

In the technique disclosed in Patent Document 2, a dermatosis such as skin roughness can be mitigated by applying β-1,3-glucan to the skin as contained in a base and the like, or by administering β-1, 3-glucan orally as contained in a food.

PRIOR ART REFERENCES

Patent Document

Patent Document 1: JP2003-529538A
Patent Document 2: JP2004-339113A

DISCLOSURE OF THE INVENTION

Problems to be Solved by the Invention

In this way, paramylon isolated from Euglena has been used in various applications and satisfactory results have been achieved therewith.

Meanwhile, the applicants of the invention have made earnest studies for further efficacious use of the paramylon isolated from Euglena.

In other words, in order to further enhance the efficacious actions that paramylon exhibits, particularly the actions of mitigating and eliminating dermatitis, the applicants have made modifications to paramylon itself and useful findings have been obtained.

In the present invention, paramylon is amorphousized to be "amorphous paramylon".

The word "amorphous" refers to a noncrystalline state of substance, where no long-range order as in a crystal is observed but a short-range order is detected.

It also refers to a thermodynamic state where a free energy is minimized (nonequilibrium metastable state).

Even in the case of same substances, physical properties of the same materials may be varied greatly between a crystalline state and an amorphous state.

For example, it is reported that electric conductivity, thermal conductivity, light permeability, physical strength, corrosion resistance, superconductivity, and the like may be varied greatly.

The present invention, which solves the above problems respectively, relates to an allergy inhibitor using the efficacy of amorphous paramylon which is obtained by changing a crystalline structure of paramylon.

Means for Solving the Problems

The above problems can be solved by an allergy inhibitor of the invention according to Claim 1, the allergy inhibitor for inhibiting an allergic disease comprising amorphous paramylon obtained by amorphousizing crystalline paramylon derived from Euglena.

In this case, the amorphous paramylon has a property of a 20% or lower of relative crystallinity to the crystallinity of the crystalline paramylon, determined by an X-ray diffractometry.

As described above, according to the present invention, crystalline paramylon is amorphousized to produce "amorphous paramylon" in order to enhance the efficacious effect.

Note that "Crystalline paramylon" refers to paramylon refined from a cultured Euglena through a known method, which is typically provided in a powder form.

In the present specification, a word "crystalline" is used to materially distinguish crystalline paramylon and "amorphous" paramylon.

As mentioned above, according to the present invention, crystalline paramylon is amorphousized to have a non-crystalline structure (wherein the "non-crystalline structure" does not mean "not to have any crystalline structure", but means "to have a less crystalline structure compared to crystalline paramylon").

Thus, the amorphous paramylon according to the present invention obtained through amorphousization has a 20% or lower of relative crystallinity to a crystallinity of crystalline paramylon determined by X-ray diffractometry.

In this way, the amorphous paramylon obtained through amorphousization becomes an efficacious substance showing different physical properties (specific gravity, crystalline size, and the like) different from those of crystalline paramylon powder, and exhibiting, in particular an allergy inhibitory effect.

Specifically, the above allergy refers to dermatitis or pollinosis, and the above dermatitis is an atopic dermatitis including both Type I sensitivity and Type IV sensitivity.

An allergy inhibitor according to the present invention with the above properties produces an efficacious allergy inhibitory action efficaciously when it is contained in at least one product selected from foodstuff, medicine, and feedstuff.

A word "contained" has a meaning "included in at least one portion as an ingredient" and also includes a meaning "composed entirely by amorphous paramylon (allergy inhibitor)" in its concept.

Thus, an allergy inhibitor comprising amorphous paramylon according to the invention is a useful substance which can be provided as any types of substance of allergy inhibitory actions, and as well, allows a wide range of applications.

Effect Of The Invention

An allergy inhibitor according to the present invention utilizes an efficacy of amorphous paramylon which is obtained by changing the crystalline structure of crystalline paramylon.

It is found that allergic symptoms are efficaciously inhibited by administering an allergy inhibitor comprising the amorphous paramylon.

Thus, an allergy inhibitor according to the present invention can be widely utilized to inhibit an allergic disease efficaciously.

DETAILED DESCRIPTION OF THE INVENTION

In the following, an embodiment of the present invention will be described based on the drawings.

The configuration described below is not intended to limit the scope of the invention, and various modifications can be made within the scope of the invention.

The present embodiment relates to amorphous paramylon which is obtained by amorphousizing crystalline paramylon for further enhancement of the efficacious effect of the crystalline paramylon.

Figure 1:
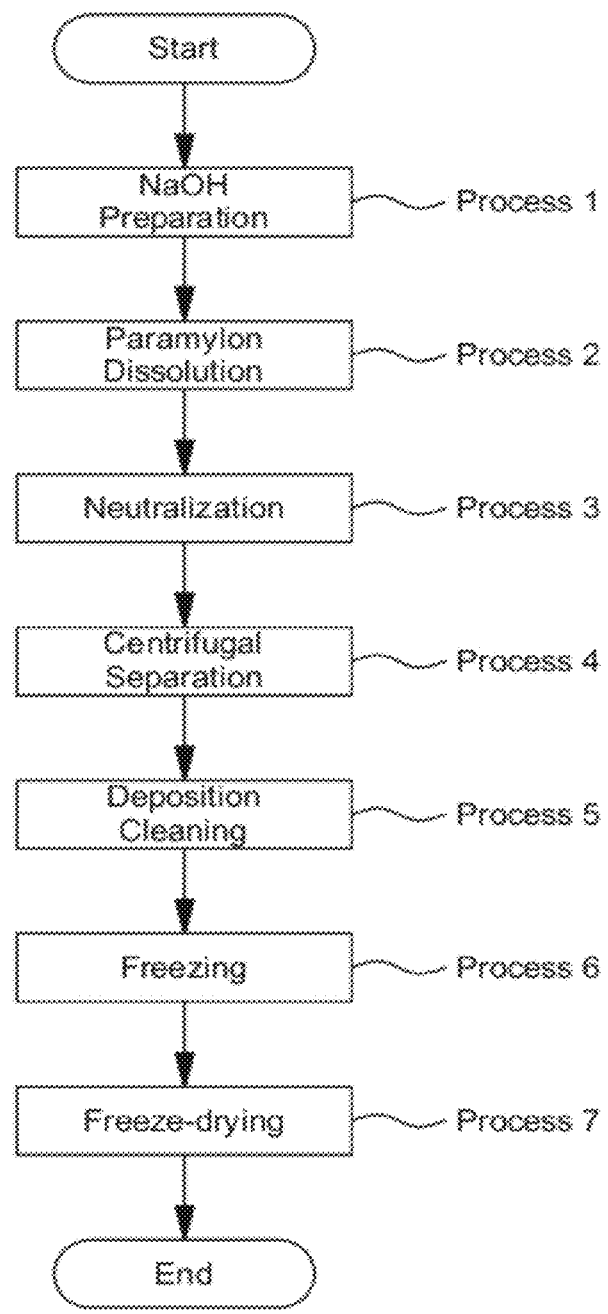
FIG. 1 is a process drawing showing a process of manufacturing amorphous paramylon according to one embodiment of the present invention.
Figure 2:
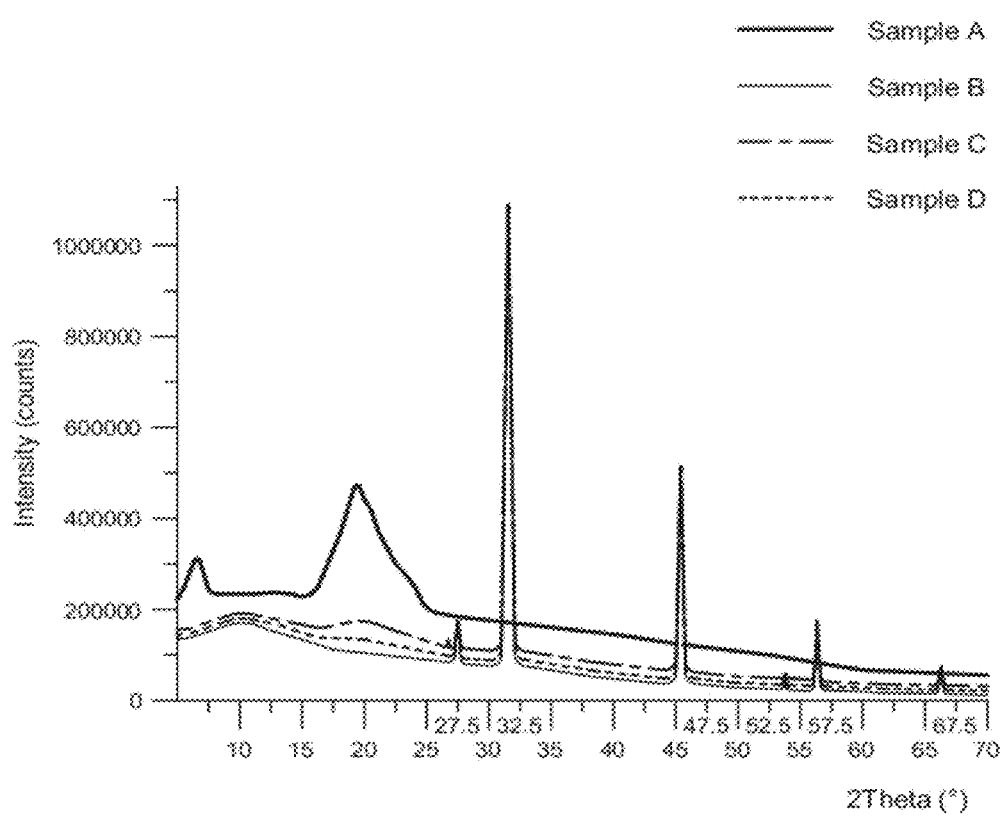
FIG. 2 is a scan chart showing a full scan result of determining a diffraction peak position of amorphous paramylon according to one embodiment of the invention.
Figure 3:
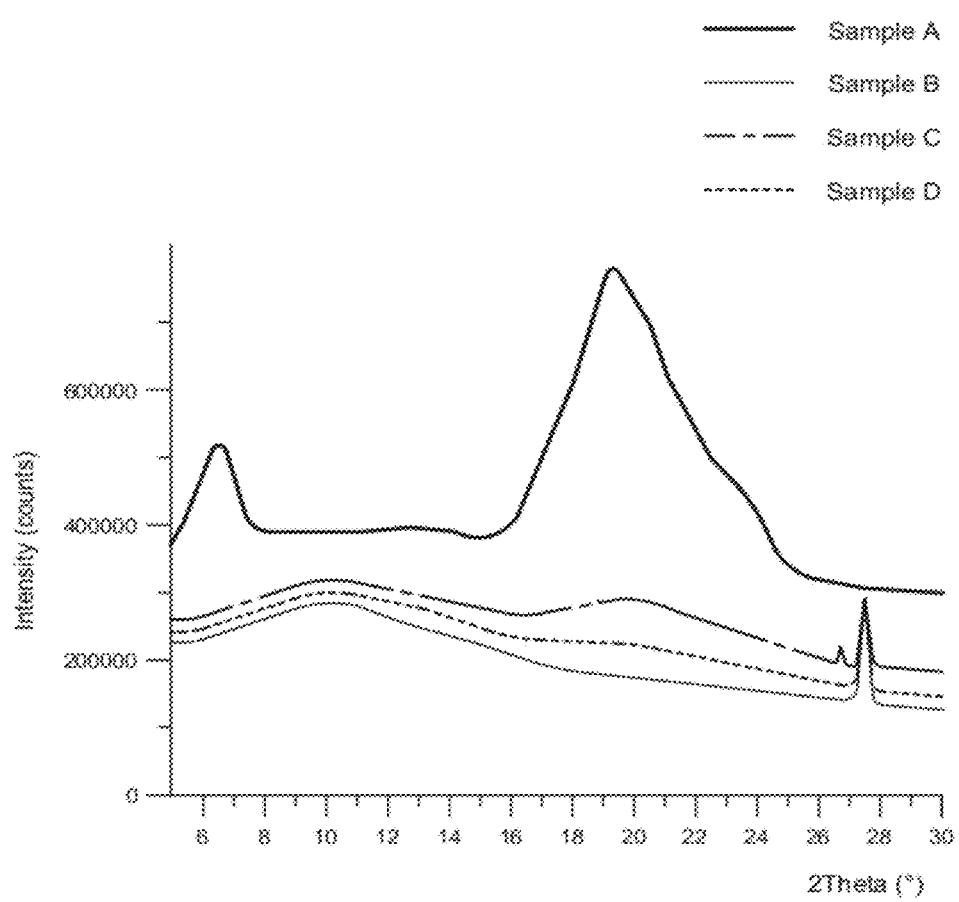
FIG. 3 is a scan chart showing a detailed scan result of determining a diffraction intensity of amorphous paramylon according to one embodiment of the present invention.
Figure 4:
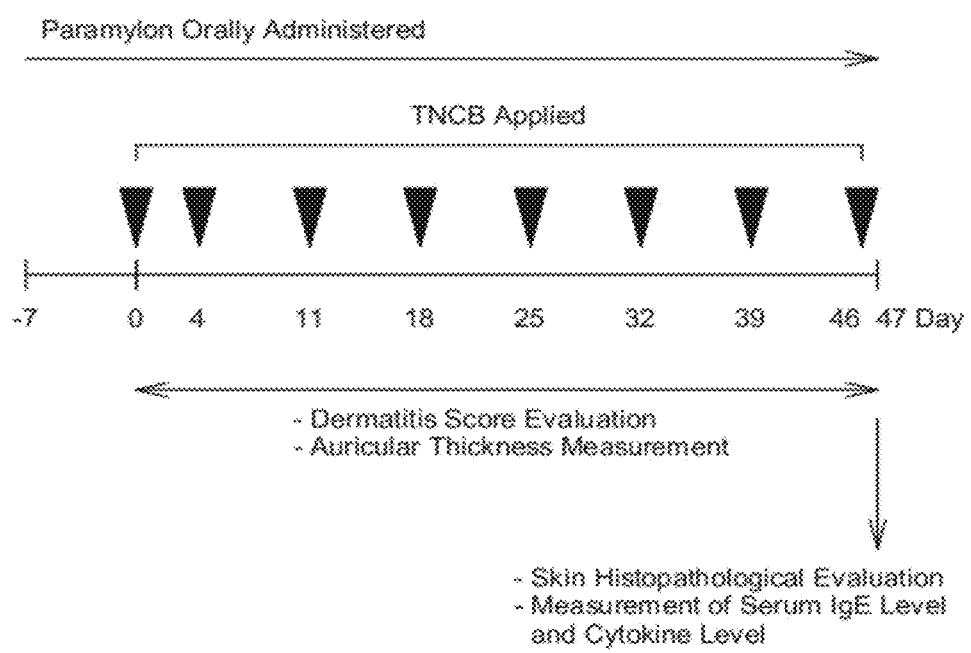
FIG. 4 is an experimental protocol.
Figure 5:
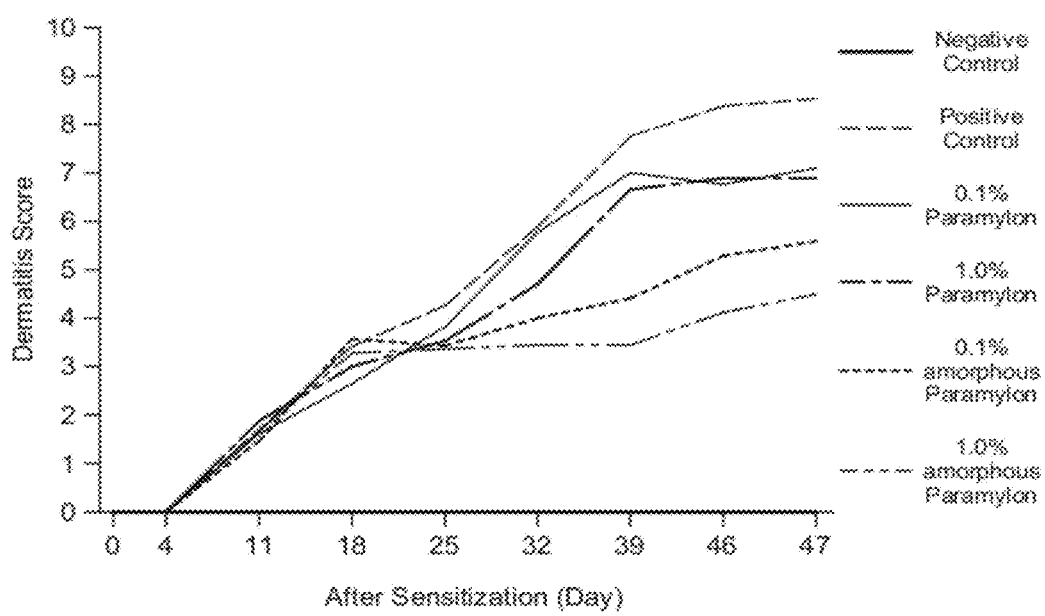
FIG. 5 is a graph showing a result of dermatitis score.
Figure 6:
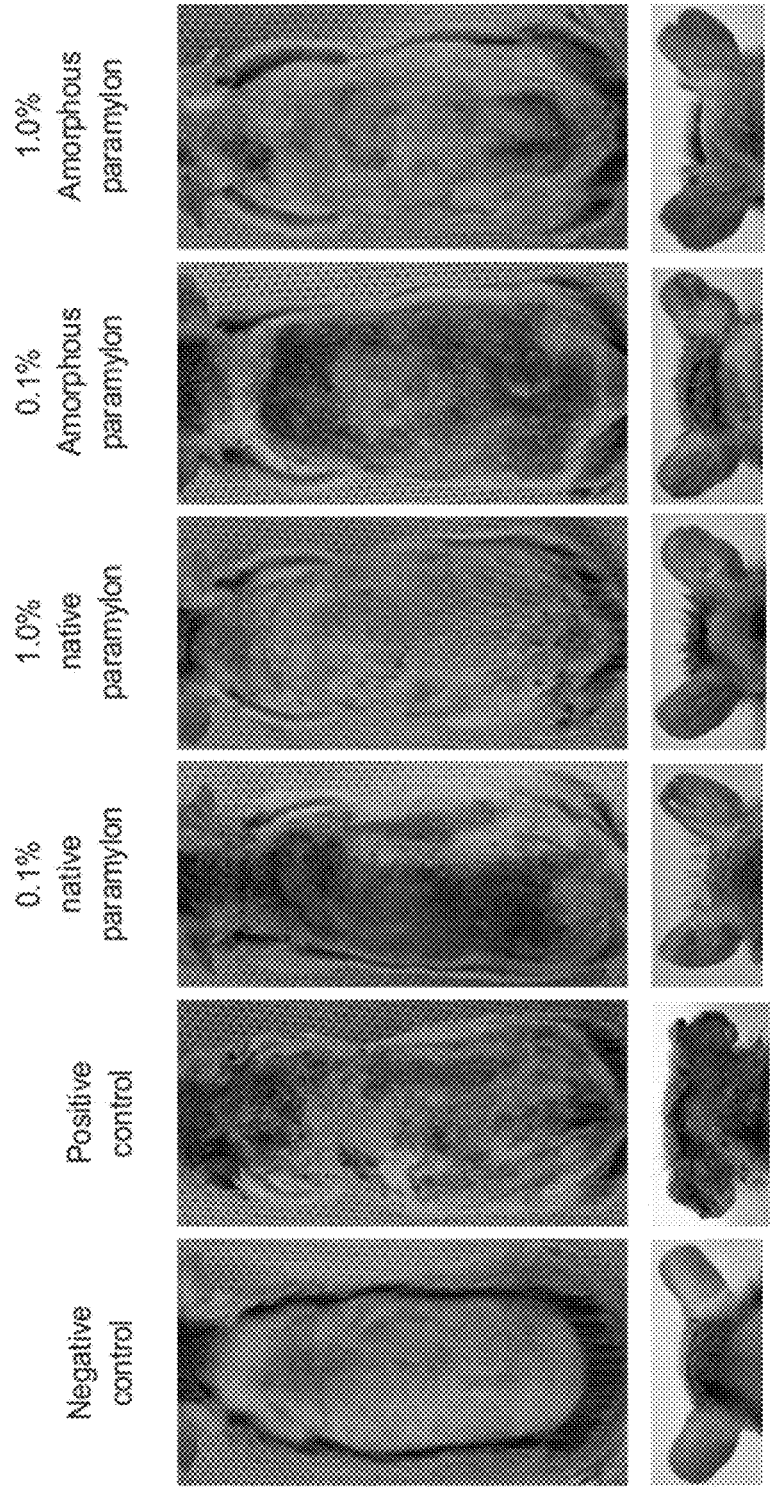
FIG. 6 is a photograph image of the conditions of the auricles and the dorsal skin.
Figure 7:
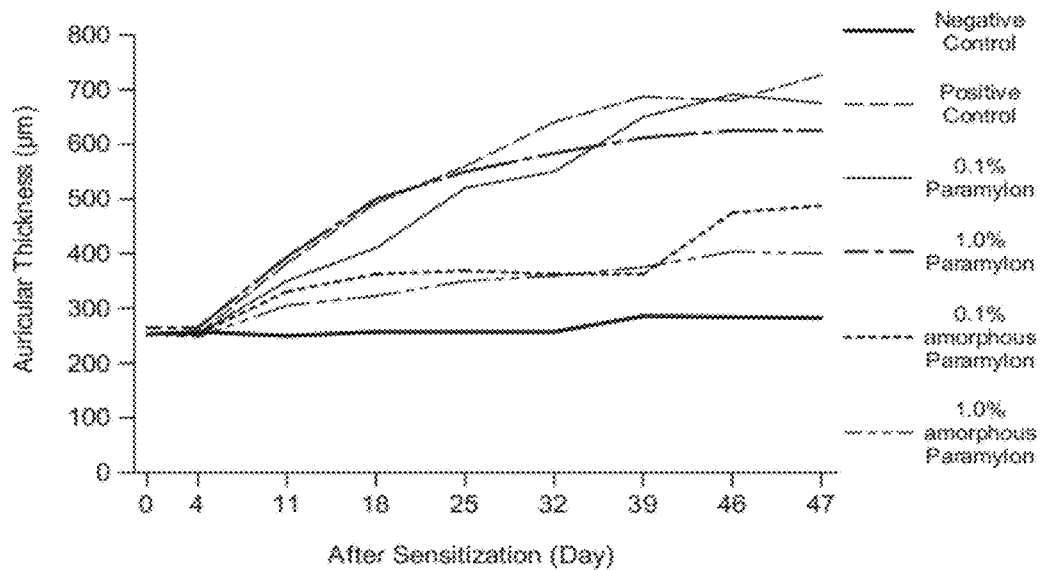
FIG. 7 is a graph showing a thickness of the auricles.
Figure 8:
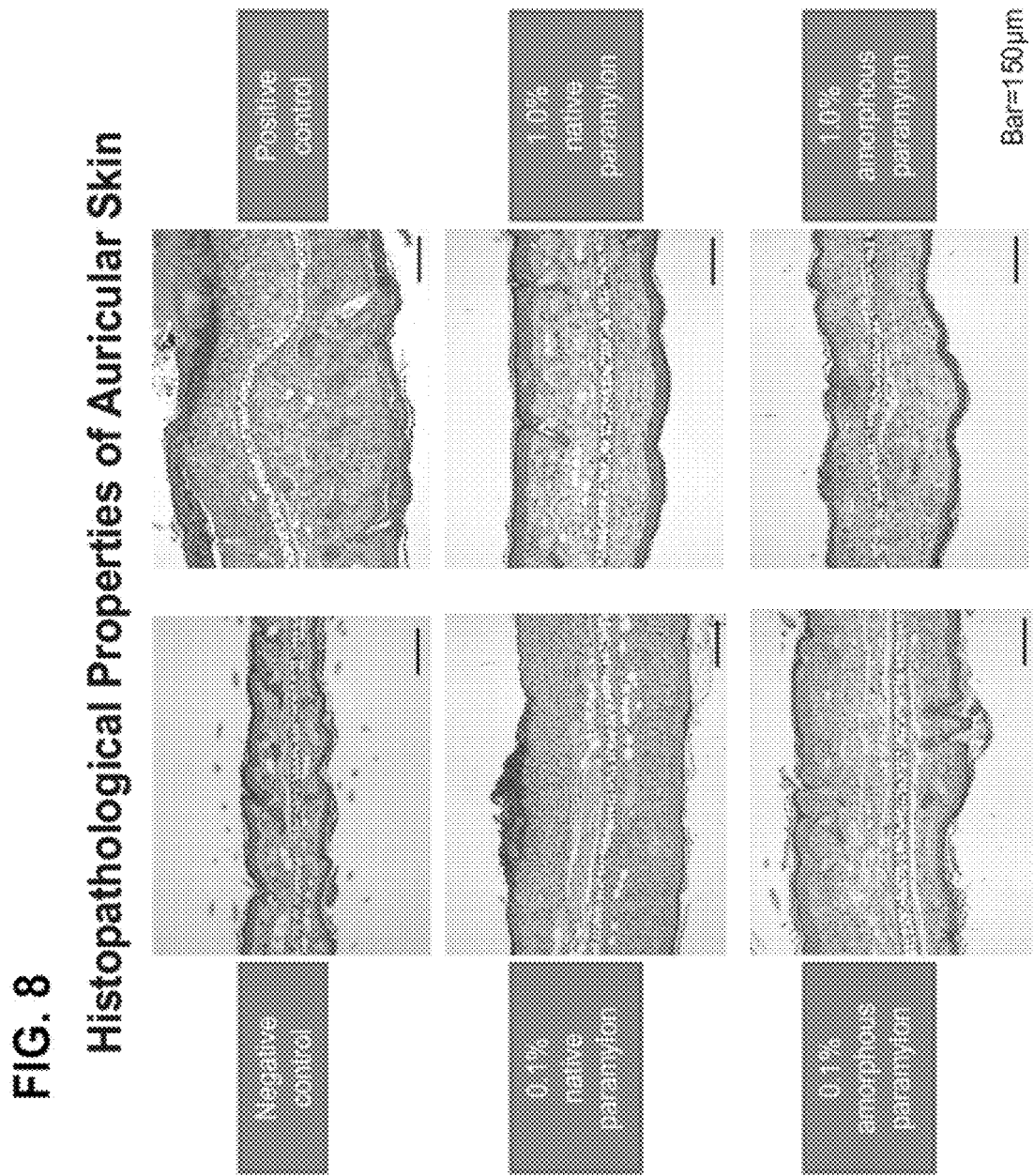
FIG. 8 is a photograph image of a histological tissue of the skin.
Figure 9:
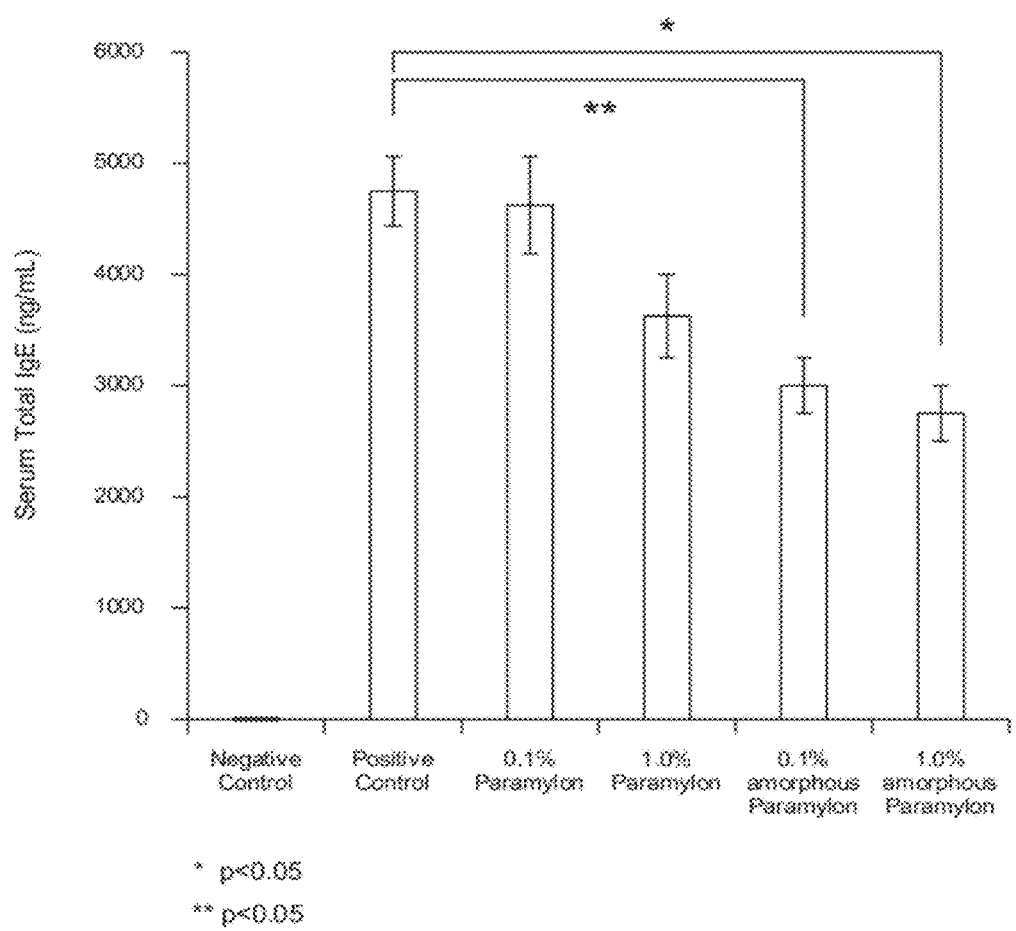
FIG. 9 is a graph showing a serum total IgE level.
Figure 10:
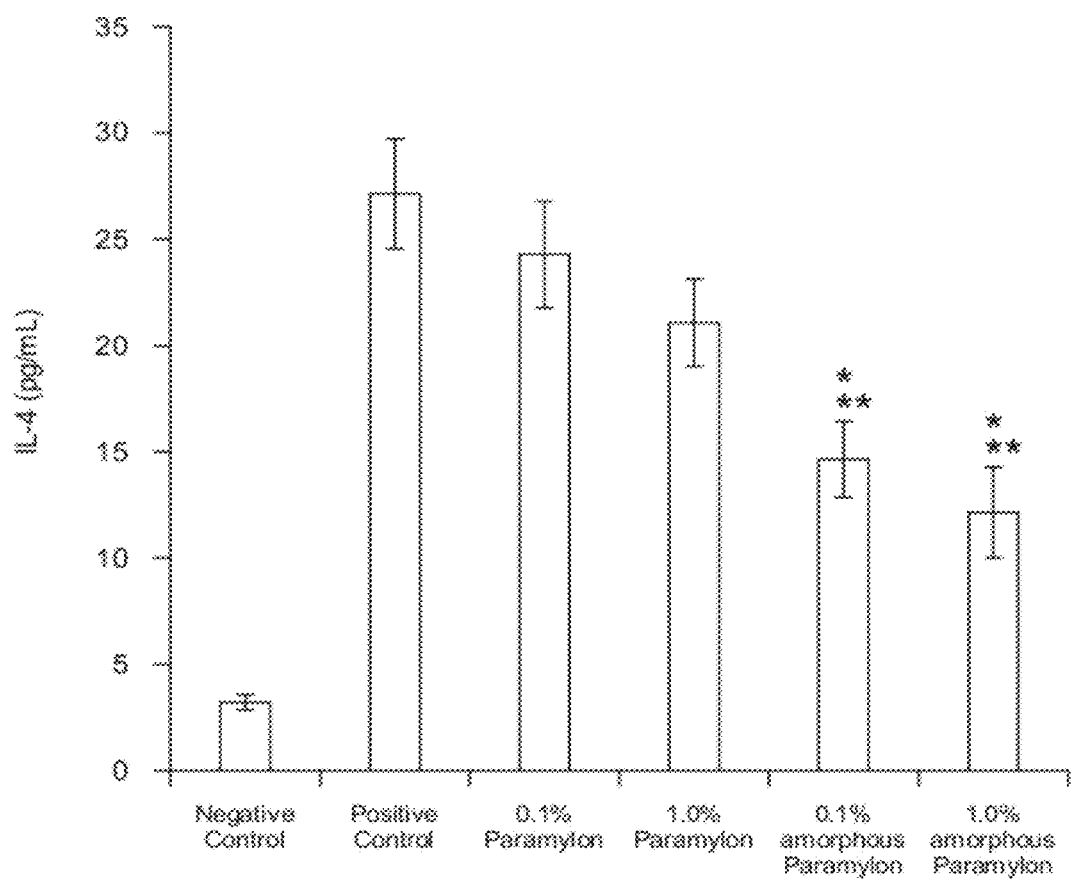
FIG. 10 is a graph showing a serum IL-4 level.
Figure 11:
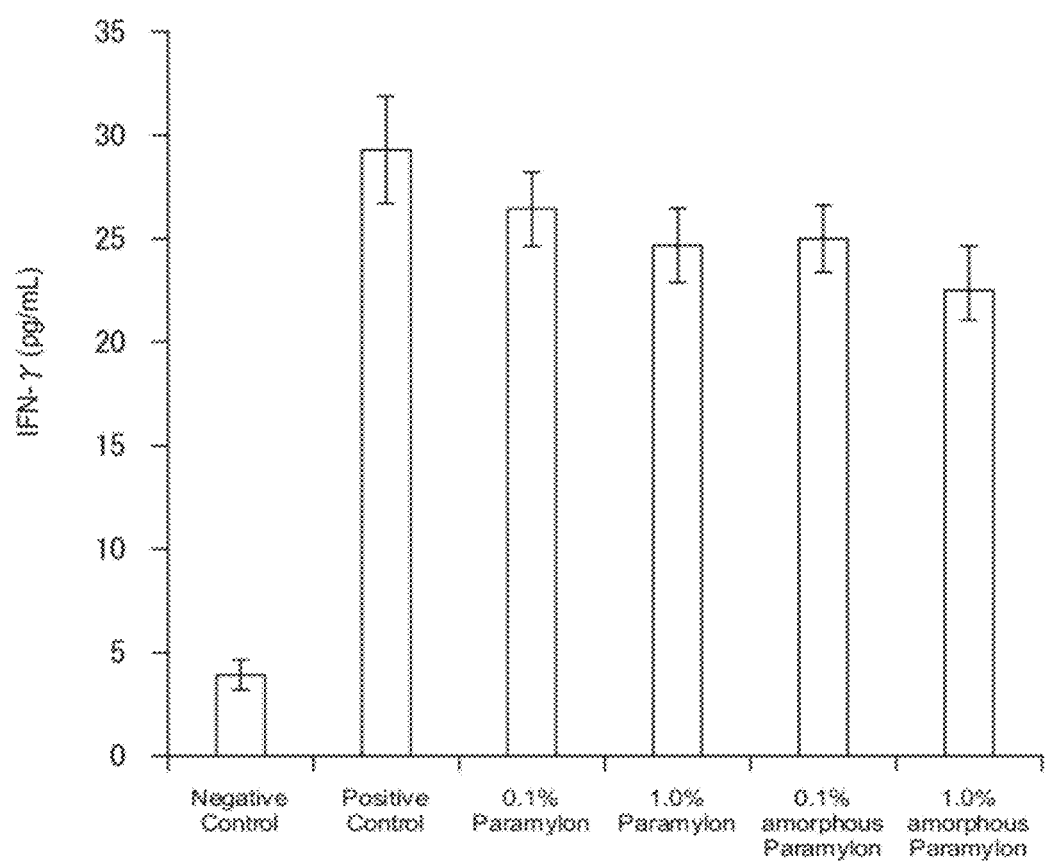
FIG. 11 is a graph showing a serum IFN-γ level.

FIG. 1 is a process drawing showing a process of manufacturing amorphous paramylon, FIG. 2 is a scan chart showing a full scan result of determining a diffraction peak position of amorphous paramylon, FIG. 3 is a scan chart showing a detailed scan result of determining a diffraction intensity of amorphous paramylon, FIG. 4 is an experiment protocol, FIG. 5 is a graph showing a result of dermatitis score, FIG. 6 is a photograph image of the conditions of the auricles and the dorsal skin, FIG. 7 is a graph showing a thickness of the auricles, FIG. 8 is a photograph image of a histological tissue of the skin, FIG. 9 is a graph showing a serum total IgE level, FIG. 10 is a graph showing a serum IL-4 level, and FIG. 11 is a graph showing a serum IFN-γ level.

A manufacturing method of amorphous paramylon will be described with reference to FIG. 1.

The manufacturing method described herein is an example for producing approximately 40 g of amorphous paramylon, and the production amount of amorphous paramylon can be incremented or decremented by suitably changing the scale. The procedures are the similar in both cases.

First, in Process 1, a 1N sodium hydroxide aqueous solution was prepared.

In the present embodiment, 2 liters of sodium hydroxide aqueous solution was prepared.

Then, in Process 2, 50 g of crystalline paramylon powders was added and dissolved in the 1N sodium hydroxide aqueous solution.

The crystalline paramylon powder was dissolved in the 1N sodium hydroxide aqueous solution through agitation by means of a stirrer for 1 to 2 hours.

This crystalline paramylon powder was isolated and refined from cultured Euglena by a well-known method.

Then, in Process 3, the 1N sodium hydroxide aqueous solution in which the paramylon powder had been dissolved was neutralized by 1N hydrochloric acid.

As the 1N hydrochloric acid was added dropwise, the part to which the solution had been added was gelled, but the neutralization reaction was continued by collapsing the gelled part with spatulas until completion of the neutralization reaction was recognized.

At the time when the neutralization reaction was completed, the water content of the mixture was completely incorporated in the gel and the entire mixture solution was gelled.

Then, in Process 4, centrifugal separation was performed to separate the water content.

The centrifugal separation may be carried out under the conditions allowing water content separation and precipitate collection.

In the present embodiment, the centrifugal separation was carried out in 100 ml centrifuge tube at 2500 rpm for 10 minutes.

Then, in Process 5, the supernatant was discarded and the precipitate was washed.

In this Process, distilled water was added to the precipitate and stirred, and then centrifugal separation was performed thereto.

In this way, a precipitate was washed to collect a precipitated gel by repeating the processes of discarding supernatant, adding distilled water, stirring, and centrifugally separating.

In the present embodiment, the above washing process was repeated four times.

Then, in Process 6, the collected gel was spread in a bat, frozen in a freezer, and freeze-dried in a lyophilizer in Process 7, to obtain amorphous paramylon.

Amorphous paramylon thus collected was partially unstiffened by hand and then stored in a desiccator with a desiccant because of its high hygroscopicity.

Through this operation, approximately 40 g of amorphous paramylon could be produced.

Then, amorphous paramylon according to the present invention will be described.

To determine a crystallinity of amorphous paramylon, X-ray diffraction was carried out on each paramylon sample.

The following samples were prepared.

(1) Samples
1. Sample A: Crystalline paramylon
2. Sample B: Amorphous paramylon (production scale of 30 g)
3. Sample C: Amorphous paramylon (production scale of 15 g)
4. Sample D: Amorphous paramylon (production scale of 5 g)

After pulverized by a crusher, these samples were analyzed using an X-ray diffractometer.

Although Sample A was a crystalline paramylon powder, the pulverization was also conducted on Sample A because Samples B to D were pulverized for making the pretreatment conditions identical.

Sample A was a control, and a relative crystallinity in amorphous paramylon samples B to D were calculated with respect to the Sample A.

(2) Pretreatment
1. Pulverizer

Ball mill MM400 manufactured by Retsch Co. Ltd. Pulverization condition: Frequency of 20 times/sec., Pulverization duration for 5 minutes 2. X-Ray Diffractometer H'PertPRO manufactured by Spectris Co., Ltd.

Measurement condition: Tube voltage of 45 KV, Tube current of 40 mA

Measuring range: $2\theta=5$-$70°$ (full scan for diffraction peak position determination)

$2\theta=5$-$30°$ (detailed scan for intensity measurement)

(3) Analysis
1. Peak Position Determination

Diffraction peak position was measured by a full scan to determine an angle to be used for a diffraction peak intensity measurement.

2. Diffraction Peak Intensity Measurement

A detailed scan was conducted at an angle decided by the above peak position determination to measure a diffraction peak intensity.

Based on the measured result, a diffraction peak intensity ratio was calculated as a relative crystallinity.

(4) Results
1. Peak Position Determination

A full scan result of diffraction peak position determination is shown in FIG. 2.

As shown in FIG. 2, in Sample A, a significant peak could be observed at around $2\theta=20°$.

Therefore, a range of detailed scan for intensity measurement was determined at around $2\theta=5°$ to $2\theta=30°$.

2. Results of Intensity Measurement

Results of detailed scan for intensity measurement are shown in FIG. 3.

As shown in FIG. 3, in Samples B to D, a diffraction peak at around $2\theta=20°$ was found to be smaller than that in Sample A, which indicates that the crystallinity in Samples B to D was reduced as compared to that in Sample A.

3. Calculation of Crystallinity

Results of the intensity measurement and results of the relative crystallinity calculation in Samples B to D of amorphous paramylon are shown in Table 1.

TABLE 1

| Sample | Diffraction peak intensity (counts) | Relative crystallinity (%) |
|---|---|---|
| A | 380771.3 | 100 |
| B | 6220.2 | 1.6 |
| C | 60968.9 | 16.0 |
| D | 21036.5 | 5.5 |

Relative crystallinity was calculated in the following equation based on the intensity measurement results.

Relative crystallinity(%)=(Diffraction peak intensity in sample/diffraction peak intensity in control)×100 i.e., a crystallinity of amorphousized paramylon was calculated by assuming a crystallinity of crystalline paramylon as a control to be 100%.

From these results, a relative crystallinity of amorphous paramylon is considered to be approximately equal to or less than 20%, more specifically be 16% or lower.

In addition, in FIG. 2 that shows the results of full scan for diffraction peak position determination, several sharp peaks are observed in the area other than at around $2\theta=20°$.

Since these sharp peaks are seen commonly in Samples B to D, it is suggested that they have the same structure. Also from this, it is suggested that a crystalline structure of paramylon was changed by amorphousization, producing a different crystalline structure from that observed in crystalline paramylon.

It is presumed that, since a triple helix structure as an original crystalline structure was disappeared after amorphousization, a peak of a steric structure instead of the helix structure β-1,3-glucan, or a peak of normal single-strand of β-1,3-glucan appeared.

As described above, amorphous paramylon can be made from crystalline paramylon by changing its crystalline structure to thereby produce an associated efficacious effect.

In other words, amorphous paramylon can exhibit a highly enhanced efficacy, which is not found in crystalline paramylon of ordinary crystalline structure or is degraded in crystalline paramylon of ordinary structure.

Next, an exemplary effect of amorphous paramylon will be described.

Model mice developing atopic dermatitis were used.

A method of experiment will be described below.

First, 5-week old NC/Nga male mice were purchased and acclimated for 1 week, and then experiments and evaluations were conducted based on a protocol shown in FIG. 4.

NC/Nga mice are animals produced for a purpose of spontaneously developing dermatitis.

Some NC/Nga mice were allowed to freely access a powder feed mixed with a prescribed amount of test substance, and the other mice were allowed to access a powder feed without test substance (positive and negative controls) every day during a study period (54 days).

7 days after administration of the test substance, the fur of the mice were removed from the abdominal and dorsal regions, 150 µl of a solution containing trinitrochlorobenzene (2,4,6-Trinitrochlorobenzene: hereinafter, abbreviated as "TNCB"), which is a substance contact-sensitized to dermatitis, was applied to the chest, abdomen, hind leg (foot pad) of the mice for inducing sensitization.

A TNCB solution, which had been prepared by dissolving a TNCB at a concentration of 5% in a mixture of 99.5% ethanol and acetone in a ratio of 4:10, was used.

After 4 days after sensitization, the TNCB solution was applied on the dorsal region and both of the right and left auricle surfaces once every other week.

130 µl of the TNCB solution was applied on the dorsal region, and 10 µl of the TNCB solution was applied to each of the auricle surfaces.

The mice were euthanized 47 days after sensitization to collect the dorsal skin, the right and left auricles, and the blood, which were then subjected to several evaluations.

Experimental groups were:
 a. Negative control (not sensitized to TNCB): Standard feed administration
 b. Positive control: Standard feed administration
 c. Administration of 0.1% crystalline paramylon (mixed in a feed)
 d. Administration of 1% crystalline paramylon (mixed in a feed)
 e. Administration of 0.1% amorphous paramylon (mixed in a feed)
 f. Administration of 1% amorphous paramylon (mixed in a feed).
 n is 10 in each case.

(1) Dermatitis Score

The results are shown in FIG. 5.

FIG. 5 shows a result of dermatitis score.

The dermatitis score is a score showing a total grading (0 to 12 points) of symptoms in 0 (no sign), 1 (minimal), 2 (moderate), 3 (serious) based on the severity of:
 a. Flare, bleeding
 b. Edema
 c. Abrasion, epidermolysis, tissue deficit
 d. Dried hide, incrustation The evaluation was performed on 0, 4, 11, 18, 25, 32, 39, 46, and 47 days after sensitization.

As seen in FIG. 5, significant dermatitis symptoms were observed in the positive control group, whereas the dermatitis symptoms were inhibited in the crystalline paramylon-dosed group and the amorphous paramylon-dosed group.

Moreover, a significant difference was observed between the positive control group and both of the crystalline paramylon-dosed group and the amorphous paramylon-dosed group (significance level 5%).

Furthermore, a significant difference was also observed between the crystalline paramylon-dosed group and the amorphous paramylon-dosed group (significance level 5%). The dermatitis symptoms were inhibited more efficaciously in the amorphous paramylon-dosed group.

(2) Auricular Hypertrophy

Auricular thickness was measured 0, 4, 11, 18, 25, 32, 39, 46, and 47 days after sensitization using a dial thickness gauge (model G-6C, manufactured by OZAKI MFG. CO., LTD.).

The results are shown in FIG. 6 (photograph) and FIG. 7.

As seen in FIG. 6, the auricles of the positive control group were thickened and deformed significantly.

This was due to a progression of the dermatitis symptoms.

On the other hand, an inhibition of the symptoms was observed in the crystalline paramylon-dosed group and the amorphous paramylon-dosed group.

This results shows that a progression of dermatitis is inhibited in the crystalline paramylon-dosed group and the amorphous paramylon-dosed group.

Furthermore, as seen in FIG. 7, an auricular thickness 47 days after sensitization is significantly different between the positive control group and 1% crystalline paramylon-dosed group, between the positive control group and both of 0.1% amorphous paramylon-dosed group and 1% amorphous paramylon-dosed group, and between both of 0.1% crystalline paramylon goosed group and 1% crystalline paramylon-dosed group, and both of 0.1% amorphous paramylon-dosed group and 1% amorphous paramylon-dosed group(significance level 5%).

Thus, it is verified that crystalline paramylon itself exhibits an inhibitory effect on dermatitis, and further amorphous paramylon, which is amorphousized, inhibits dermatitis more effectively.

(3) Histopathological Finding of the Skin

Paraffin-embedded skin sections of each group were prepared and stained with hematoxylin and eosin.

The results are shown in FIG. 8 (photograph).

As shown in FIG. 8, no apparent histopathological change was observed in the negative control group, whereas epidermal hypertrophy, hyperkeratosis, and an infiltration of inflammatory cells such as eosinophil, mast cell, and lymphocyte to the dermis was observed in the positive control group.

An alleviation in the histological symptoms was observed in the crystalline paramylon-dosed group and the amorphous paramylon-dosed group.

This effect was more significant in the amorphous paramylon-dosed group than the crystalline paramylon-dosed group, and moreover, in both groups, the groups dosed at the concentration of 1% shows a more significant effect than those dosed at 0.1%.

(4) Serum Total IgE Level

Measurement through ELISA method was performed using a Mouse IgE Measurement Kit (product name: YSE-7675, manufactured by COSMO BIO Co., Ltd.).

The results are shown in FIG. 9.

A significant increase of serum IgE levels was observed in the positive control group, whereas an increase of serum IgE levels was inhibited the crystalline paramylon-dosed group and the amorphous paramylon-dosed group.

A significant difference was observed between the positive control group and both of the 0.1% amorphous paramylon-dosed group and the 1% amorphous paramylon-dosed group (significance level 5%), and an increase of serum IgE levels was suppressed in the amorphous paramylon-dosed group.

This result suggests that amorphous paramylon efficaciously inhibits atopic dermatitis, particularly Type I hypersensitivity.

In other words, since Type I hypersensitivity in atopic dermatitis is an inflammatory reaction caused by a degranulation of a mast cell in the peripheral tissue where a Th2 Type CD4+T cell moved to a lymph node was sensitized with IgE of B cell, it is also suggested that amorphous paramylon enables inhibition of this symptom by reducing IgE levels.

This result further suggests that amorphous paramylon is effective for inhibition of an allergic disease such as pollinosis.

That is, it is suggested that amorphous paramylon suppresses an increase of serum. IgE level to thereby reduce IgE which binds with pollen allergen, which indicates that amorphous paramylon is effective for inhibiting allergic symptoms.

In other words, it is suggested that amorphous paramylon has an immunomodulatory function and shows an effect for mitigating symptoms of Type I hypersensitivity in atopic dermatitis and pollinosis in human.

(5) Serum Cytokine

Levels of serum cytokines, i.e. serum IL-4 levels and serum IFN-$\gamma$ levels were determined.

The results are shown in FIGS. 10 and 11.

As shown in FIG. 10, a significant increase of serum IL-4 levels was observed in the positive control group, whereas an increase of serum IL-4 levels was suppressed in the crystalline paramylon-dosed group and the amorphous paramylon-dosed group.

A significant difference was observed between the positive control group and both of the 0.1% amorphous paramylon-dosed group and the 1% amorphous paramylon-dosed group (significance level 5%), which indicates that an increase of serum IL-4 levels was suppressed in the amorphous paramylon-dosed group.

As shown in FIG. 11, a significant increase of serum IFN-$\gamma$ levels was observed in the positive control group.

In each of the crystalline paramylon-dosed group and each of the amorphous paramylon-dosed group, serum IFN-$\gamma$ levels tends to decrease, but no statistically significant difference was observed between them.

However, as shown in FIG. 11, since the serum IFN-$\gamma$ levels tend to decrease, it is considered that crystalline paramylon and amorphous paramylon have an effect for inhibiting the increase of serum IFN-$\gamma$ level.

This result suggests that amorphous paramylon efficaciously inhibits Type IV hypersensitivity in atopic dermatitis.

In other words, it is suggested that, in the case of Type IV hypersensitivity in atopic dermatitis, in which an infiltration of Th2 Type CD4+T cell to a skin lesion area causes an inflammation due to production of cytokine, amorphous paramylon reduces the cytokine level and efficaciously inhibits Type IV hypersensitivity in atopic dermatitis.

Thus, it is verified that crystalline paramylon itself shows an inhibitory effect on each allergic disease, but amorphous paramylon shows a higher inhibitory effect on each allergic disease compared to those produced by such an ordinary crystalline paramylon.

In this way, amorphous paramylon obtained through amorphousization realizes an effect which can not been seen in an ordinary crystalline paramylon.

In other words, it is verified that amorphous paramylon acts as an allergy inhibitor that efficaciously inhibits an allergic disease.

In the present embodiment, although amorphous paramylon is administered orally, the way of administration is not limited to this, and various way of administration can be applied without departing from the spirit or scope of the present invention.

In other words, in addition to the use as a medicine, amorphous paramylon can be used as a health food in combination with other materials and further applications as a feedstuff or the like may be envisioned.

As described above, amorphous paramylon allows a wide variety of applications as an allergy inhibitor.

What is claimed is:

1. A method for inhibiting or treating an allergic disease comprising administering an effective amount of an amorphous paramylon compound having 20% or lower relative crystallinity to a subject in need thereof, wherein the amorphous paramylon compound is obtained by amorphosizing crystalline paramylon.

2. The method according to claim 1, wherein the allergic disease is dermatitis or pollenosis.

3. The method according to claim 2, wherein the allergic disease is atopic dermatitis selected from Type I hypersensitivity and/or Type IV hypersensitivity.

* * * * *